United States Patent
Saito et al.

(10) Patent No.: US 10,758,484 B2
(45) Date of Patent: Sep. 1, 2020

(54) CED OF SN-38-LOADED MICELLES AGAINST BRAIN TUMOR

(71) Applicant: Nippon Kayaku Co., Ltd., Tokyo (JP)

(72) Inventors: Ryuta Saito, Sendai (JP); Teiji Tominaga, Sendai (JP)

(73) Assignee: Nippon Kayaku Co., Ltd., Tokyo (JP)

( * ) Notice: Subject to any disclaimer, the term of this patent is extended or adjusted under 35 U.S.C. 154(b) by 397 days.

(21) Appl. No.: 15/505,711

(22) PCT Filed: Aug. 24, 2015

(86) PCT No.: PCT/IB2015/001683
§ 371 (c)(1),
(2) Date: Feb. 22, 2017

(87) PCT Pub. No.: WO2016/030748
PCT Pub. Date: Mar. 3, 2016

(65) Prior Publication Data
US 2018/0214375 A1     Aug. 2, 2018

Related U.S. Application Data

(60) Provisional application No. 62/041,372, filed on Aug. 25, 2014.

(51) Int. Cl.
| | | |
|---|---|---|
| A61K 9/107 | (2006.01) |
| A61K 9/00 | (2006.01) |
| A61K 47/34 | (2017.01) |
| A61K 31/4745 | (2006.01) |
| A61P 35/00 | (2006.01) |

(52) U.S. Cl.
CPC .......... *A61K 9/1075* (2013.01); *A61K 9/0085* (2013.01); *A61K 9/107* (2013.01); *A61K 31/4745* (2013.01); *A61K 47/34* (2013.01); *A61P 35/00* (2018.01)

(58) Field of Classification Search
None
See application file for complete search history.

(56) References Cited

FOREIGN PATENT DOCUMENTS

| | | |
|---|---|---|
| JP | 2002-516295 A | 6/2002 |
| JP | 2009-137884 A | 6/2009 |
| WO | WO-2007/127839 A | 11/2007 |

OTHER PUBLICATIONS

Machine translation, JP 2009-137884 (2009).*
Wang et al., "Effective conversion of irinotecan to SN-38 after intratumoral drug delivery to an intracranial murine glioma model in vivo", J Neurosurg, vol. 114, pp. 689-694 (2011).*
Kawano et al., "Enhanced antitumor effect of camptothecin loaded in long-circulating polymeric micelles", J. Controlled Release, 112, pp. 329-332 (2006).*

(Continued)

*Primary Examiner* — Bethany P Barham
*Assistant Examiner* — Barbara S Frazier
(74) *Attorney, Agent, or Firm* — Leason Ellis LLP

(57) ABSTRACT

The present invention discloses a method for administering SN-38-loaded polymeric micelles into the central nervous system of a human subject via a convection-enhanced delivery system. The convection-enhanced delivery is achieved by using an osmotic pump or an infusion pump. Further, SN-38-loaded polymeric micelles are administered into a target region of the brain of the subject.

9 Claims, 7 Drawing Sheets

(56) References Cited

OTHER PUBLICATIONS

Zhang et al., "Convection-enhanced delivery of SN-38-loaded polymeric micelles (NK012) enables consistent distribution of SN-38 and is effective against rodent intracranial brain tumor models", *Drug Delivery*, Oct. 8, 2016, pp. 2780-2786.
Noble et al., "Novel nanoliposomal CPT-11 infused by convestion-enhanced delivery in intracranial tumors: pharmacology and efficacy", *Cancer Research*, Mar. 1, 2006, pp. 2801-2806.
Thomale et al., "Local chemotherapy in the rat brainstem with multiple catheters: a feasibility study", *Child's Nervous System*, Aug. 9, 2008, pp. 21-28.
Extended European Search Report dated Dec. 20, 2017 for the corresponding European Patent Application No. 15835806.9.
International Preliminary Report on Patentability including Written Opinion dated Feb. 28, 2017 for the corresponding PCT Application No. PCT/IB2015/001683.
Groothuis "The blood-brain and blood-tumor barriers: a review of strategies for increasing drug delivery" *Neuro Oncology*, Jan. 2000; 2(1); p. 45-59.
Huynh et al. "Barriers to carrier mediated drug and gene delivery to brain tumors", *J Control Release*, Jan. 2006;110 (2): pp. 236-259.
Bobo et al. "Convection-enhanced delivery of macromolecules in the brain" *Proc Natl Acad Sci U S A*. Mar. 1994;91(6): pp. 2076-2080.
Chen et al. "Variables affecting convection-enhanced delivery to the striatum: a systematic examination of rate of infusion, cannula size, infusate concentration, and tissue-cannula sealing time", *J Neurosurg*, Feb. 1999;90(2): pp. 315-320.
Yun et al. "Convection-enhanced delivery for targeted delivery of antiglioma agents: the translational experience", *Journal of Drug Delivery*, 2013;2013:107573.
Eberling et al. "Results from a phase I safety trial of hAADC gene therapy for Parkinson disease", *Neurology*, May 20, 2008;70 (21): pp. 1980-1983.
Gill et al. "Direct brain infusion of glial cell line-derived neurotrophic factor in Parkinson disease", Nat Med. May 2003;9 (5): pp. 589-595.
Kunwar et al. "Convection enhanced delivery of IL13-PE38QQR for treatment of recurrent malignant glioma: presentation of interim findings from ongoing phase 1 studies", *Acta Neurochir Suppl.*, 2003;88: pp. 105-111.
Mardor et al. "Monitoring response to convection-enhanced taxol delivery in brain tumor patients using diffusion-weighted magnetic resonance imaging", *Cancer Research*, Jul. 1, 2001;61(13): pp. 4971-4973.
Sawamura et al. "Recent advances in the treatment of central nervous system germ cell tumors", *Adv Tech Stand Neurosur*, 1999;25: pp. 141-159.
Koizumi et al. "Novel SN-38-incorporating polymeric micelles, NK012, eradicate vascular endothelial growth factor-secreting bulky tumors", *Cancer Res.*, Oct. 15, 2006;66(20): pp. 10048-10056.
Matsumura "Preclinical and clinical studies of NK012, an SN-38-incorporating polymeric micelles, which is designed based on EPR effect" Advanced Drug Delivery Reviews Mar. 2011;63(3):184-192.
Kuroda et al. "Potent antitumor effect of SN-38-incorporating polymeric micelle, NK012, against malignant glioma" *Int J Cancer*, 2009;124(11), pp. 2505-2511.
Kuroda et al. "Antitumor effect of NK012, a 7-ethyl-10-hydroxycamptothecin-incorporating polymeric micelle, on U87MG orthotopic glioblastoma in mice compared with irinotecan hydrochloride in combination with bevacizumab" *Clin Cancer Res.*, Jan. 15, 2010;16(2): pp. 521-529.
Saito et al. "Convection-enhanced delivery of tumor necrosis factor-related apoptosis-inducing ligand with systemic administration of temozolomide prolongs survival in an intracranial glioblastoma xenograft model" *Cancer Res.*, Oct. 1, 2004;64(19): pp. 6858-6862.
Saito et al. "Distribution of liposomes into brain and rat brain tumor models by convection-enhanced delivery monitored with magnetic resonance imaging" *Cancer Res*. Apr. 1, 2004;64(7): pp. 2572-2579.
Kikuchi et al. "Convection-enhanced delivery of polyethylene glycol-coated liposomal doxorubicin: characterization and efficacy in rat intracranial glioma models" *J Neurosurg* Nov. 2008;109(5):pp. 867-873.
Kunwar et al, "Precise Study Group. Phase III randomized trial of CED of IL13-PE38QQR vs Gliadel wafers for recurrent glioblastoma" *Neuro Oncol.*, Aug. 2010;12(8): pp. 871-881.
Sampson et al "Precise Trial Investigators. Poor drug distribution as a possible explanation for the results of the Precise trial" *J Neurosurg*. Aug. 2010;113(2): pp. 301-309.
Saito et al. "Tissue affinity of the infusate affects the distribution volume during convection-enhanced delivery into rodent brains: implications for local drug delivery" *J Neurosci Methods*. 2006;154(1-2):225-232.
Inoue et al. "Therapeutic efficacy of a polymeric micellar doxorubicin infused by convection-enhanced delivery against intracranial 9L brain tumor models" *Neuro Oncol.*, Apr. 2009;11(2): pp. 151-157.
Friedman et al. "Irinotecan therapy in adults with recurrent or progressive malignant glioma" *J Clin Oncol*. May 1999;17(5):pp. 1516-1525.
Cloughesy et al. "Two studies evaluating irinotecan treatment for recurrent malignant glioma using an every-3-week regimen" *Cancer*, May 1, 2003;97(9 Suppl): pp. 2381-2386.
Chamberlain "Salvage chemotherapy with CPT-11 for recurrent glioblastoma multiforme" *J Neurooncol*. 2002;56(2):183-188.
Prados et al "North American Brain Tumor Consortium. A phase 2 trial of irinotecan (CPT-11) in patients with recurrent malignant glioma: a North American Brain Tumor Consortium study" *Neuro Oncol*. Apr. 2006;8(2):pp. 189-193.
Zhang et al. "Concentration rather than dose defines the local brain toxicity of agents that are effectively distributed by convection-enhanced delivery" *J Neurosci Methods*, 2013;222: pp. 131-137.
Kuroda et al., DDS in the therapy of malignant glioma, Drug Delivery System, May 28, 2010, vol. 25, No. 3, pp. 241.
Kuroda et al., "SN38 incorporating micelle, NK012, enhance the antitumor activity of SN38 in ortheotopic glioblastoma compared to CPT-11" Annual Meeting of the Japanese Cancer Association, Sep. 30, 2008, vol. 67, pp. 316.
Yokosawa et al., "Convection-Enhanced Delivery of a Synthetic Retinoid Am80, Loaded into Polymeric Micelles, Prolongs the Survival of Rats Bearing Intracranial Glioblastoma Xenografts", *Tohoku J. Exp. Med*, 2010, vol. 221, pp. 257-264.
Saito et al., "Convection-Enhanced Delivery: From Mechanisms to Clinical Drug Delivery for Diseases of the Central Nerveous System", *Neurol Med Chir (Tokyo)*, Aug. 8, 2012, vol. 52, pp. 531-538.
Saito et al., "Convection-Enhanced Delivery in glioma", *Jpn J Cancer Chemother*, Jun. 2013, pp. 705-707, vol. 40, No. 6.
International Search Report dated Jan. 19, 2016 for the corresponding PCT Application No. PCT/IB2015/001683.
Kuroda et al., DDS in the therapy of malignant glioma, Drug Delivery System, May 28, 2010, vol. 25, No. 3, pp. 241 (See cited documents CC and CD for relevancy of the document).
Saito et al., "Convection-Enhanced Delivery in glioma", Jpn J Cancer Chemother, Jun. 2013, pp. 705-707, vol. 40, No. 6 (See cited documents CC and CD for relevancy of the document).
Office Action dated Mar. 26, 2019 for the corresponding Japanese Patent Application No. 2017-511261.
English Translation of Response to Japanese Office Action dated Mar. 26, 2019.

\* cited by examiner x20　　　　　x100　　　　　x200

CED OF SN-38-LOADED MICELLES AGAINST BRAIN TUMOR

CROSS-REFERENCE TO RELATED PATENT APPLICATIONS

This application is a U.S. National Phase Application under 35 U.S.C. § 371 of International Patent Application No. PCT/IB2015/001683, filed Aug. 24, 2015, and claims the benefit of U.S. Provisional Application No. 62/041,372, filed Aug. 25, 2014, all of which are incorporated by reference in their entireties herein. The International Application was published on Mar. 3, 2016 as International Publication No. WO/2016/030748 under PCT Article 21(2).

FIELD OF THE INVENTION

The present invention relates generally to an efficient delivery of SN-38-loaded polymeric micelles to the central nervous system (CNS) of a human. In particular, the present invention relates to chemotherapy for the treatment of an intracranial brain tumor, more particularly malignant gliomas.

BACKGROUND OF THE INVENTION

Malignant brain tumors, such as glioblastoma, remain the most difficult neoplasms to treat despite intensive multimodal treatment including surgical resection, radiation therapy, and systemic chemotherapy. Systemic chemotherapy requires high doses of many anticancer drugs because of poor penetration of the blood-brain barrier (see Groothuis D R. The blood-brain and blood-tumor barriers: a review of strategies for increasing drug delivery. *Neuro Oncol.* 2000; 2(1):45-59. Also, see Huynh G H, Deen D F, Szoka F C Jr. Barriers to carrier mediated drug and gene delivery to brain tumors. *J Control Release.* 2006; 110(2): 236-259). Consequently, systemic side effects are the limiting factor in chemotherapeutic protocols for patients with brain tumor, and emphasize the need for efficient, specific methods of delivery in the treatment of human glioblastoma.

Convection-enhanced delivery (CED) is a delivery system that circumvents the blood-brain barrier by delivering agents directly into the tumor and surrounding parenchyma based on continuous positive-pressure infusion (see Bobo R H, Laske D W, Akbasak A, Morrison P F, Dedrick R L, Oldfield E H. Convection-enhanced delivery of macromolecules in the brain. *Proc Natl Acad Sci USA.* 1994; 91(6): 2076-2080). CED can achieve large volumes of distribution, as it is driven not only by the diffusive spread derived from concentration gradients, but also by continuous positive-pressure infusion (see Chen M Y, Lonser R R, Morrison P F, Governale L S, Oldfield E H. Variables affecting convection-enhanced delivery to the striatum: a systematic examination of rate of infusion, cannula size, infusate concentration, and tissue-cannula sealing time. *J Neurosurg.* 1999; 90(2):315-320). Importantly, CED provides direct access to the tumor bed, thus resulting in high local concentrations of drug with minimal systemic absorption (see Yun J, Rothrock R J, Canoll P, Bruce J N. Convection-enhanced delivery for targeted delivery of antiglioma agents: the translational experience. *J Drug Deliv.* 2013; 2013:107573). Currently, CED has been clinically tested in the treatment of neurodegenerative diseases, such as Parkinson's disease (see Eberling J L, Jagust W J, Christine C W, et al. Results from a phase I safety trial of hAADC gene therapy for Parkinson disease. *Neurology.* 2008; 70(21):1980-1983. Also, see Gill S S, Patel N K, Hotton G R, et al. Direct brain infusion of glial cell line-derived neurotrophic factor in Parkinson disease. *Nat Med.* 2003; 9(5):589-595), and neuro-oncology (see Kunwar S. Convection enhanced delivery of IL13-PE38QQR for treatment of recurrent malignant glioma: presentation of interim findings from ongoing phase 1 studies. *Acta Neurochir Suppl.* 2003; 88:105-111. Also, see Mardor Y, Roth Y, Lidar Z, et al. Monitoring response to convection-enhanced taxol delivery in brain tumor patients using diffusion-weighted magnetic resonance imaging. *Cancer Res.* 2001; 61(13):4971-4973).

SUMMARY OF THE INVENTION

Technical Problem

However, the administration of therapeutic agents via CED has various challenges including an accurate and consistent delivery of the agent (see Sawamura Y, Shirato H, de Tribolet N. Recent advances in the treatment of central nervous system germ cell tumors. *Adv Tech Stand Neurosurg.* 1999; 25:141-159). Thus, the inventors of the present invention have focused on the design of new therapeutic agents delivered by CED that can provide a reproducible delivery profile and can improve the prognosis without causing dose-limiting systemic or neurological toxicity.

Solution to Problem

NK012 is a novel SN-38-loaded polymeric micelle constructed in an aqueous medium by self-assembly of an amphiphilic block copolymer, poly (ethylene glycol)-poly (amino acid) (SN-38) (see Koizumi F, Kitagawa M, Negishi T, et al. Novel SN-38-incorporating polymeric micelles, NK012, eradicate vascular endothelial growth factor-secreting bulky tumors. *Cancer Res.* 2006; 66(20):10048-10056). SN-38 is an active metabolite of irinotecan, which is an analog of camptothecin. NK012 is categorized as a drug delivery system and several preclinical and clinical studies have shown that the formulation appears to accumulate selectively and persists for a long time in solid tumor tissues due to the enhanced permeability and retention effect (see Matsumura Y. Preclinical and clinical studies of NK012, an SN-38-incorporating polymeric micelles, which is designed based on EPR effect. *Adv Drug Deliv Rev.* 2011; 63(3):184-192). Systemically administered NK012 has antitumor activity against brain tumors (see Kuroda J, Kuratsu J, Yasunaga M, Koga Y, Saito Y, Matsumura Y. Potent antitumor effect of SN-38-incorporating polymeric micelle, NK012, against malignant glioma. *Int J Cancer.* 2009; 124(11):2505-2511. Also, see Kuroda J, Kuratsu J, Yasunaga M, et al. Antitumor effect of NK012, a 7-ethyl-10-hydroxycamptothecin-incorporating polymeric micelle, on U87MG orthotopic glioblastoma in mice compared with irinotecan hydrochloride in combination with bevacizumab. *Clin Cancer Res.* 2010; 16(2):521-529), but no optimal methods for initial local brain delivery have been established.

The inventors compared the distribution profile and therapeutic effect of NK012 delivered by CED on rodent orthotopic brain tumor models, and found that NK012 via CED significantly prolonged survival in rodent brain tumor models.

According to a first aspect of the present invention, there is provided a method for delivering SN-38-loaded polymeric micelles to a subject, comprising the step of administering the SN-38-loaded polymeric micelles into a central nervous system of the subject via a convection-enhanced delivery system. In this aspect, the convection-enhanced delivery system is an osmotic pump or an infusion pump. The subject is a human. In addition, the SN-38-loaded polymeric micelles are administered into a target region of the brain of the subject.

According to a second aspect of the present invention, there is provided a method for delivering SN-38-loaded polymeric micelles to a subject having an intracranial brain tumor, comprising the step of administering the SN-38-loaded polymeric micelles into a central nervous system of the subject via a convection-enhanced delivery system, wherein the SN-38-loaded polymeric micelles comprise SN-38 and block copolymer. In this aspect, the intracranial brain tumor is a malignant glioma. In addition, the SN-38-loaded polymeric micelles are administered into a target region of the brain of the subject.

According to a third aspect of the present invention, there is provided a method for treating an intracranial brain tumor in a subject, said method comprising the steps of: (a) providing a preparation comprising SN-38-loaded polymeric micelles; and (b) delivering the preparation to a central nervous system of the subject via a convection-enhanced delivery system, wherein the SN-38-loaded polymeric micelles release SN-38, which provides a therapeutic effect in the subject suitable for treating the intracranial brain tumor. In this aspect, the intracranial brain tumor is a malignant glioma.

According to a fourth aspect of the present invention, there is provided a method for using a convection-enhanced delivery system in a subject, comprising the step of delivering a preparation containing SN-38-loaded polymeric micelles to a cranial cavity of the subject. In this aspect, the convection-enhanced delivery is an osmotic pump or an infusion pump.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIG. 2A is an image showing the distribution of free SN-38 (0.2 mg/ml; 20 μl) infused by CED into the striatum of rat brains. FIG. 2B is an image showing the distribution of NK012 (0.2 mg/ml; 20 μl) infused by CED into the striatum of rat brains. FIG. 2C is a chart showing mean volumes of distribution after NK012 and free SN-38 are infused.

FIG. 4A indicates an outcome for rats bearing 9L tumors with single CED infusions of 5% glucose, free SN-38, and NK012. FIG. 4B indicates an outcome for animals implanted with U87MG tumor cells and which received NK012 on day 5 after tumor implantation.

DETAILED DESCRIPTION OF THE INVENTION

Figure 1:
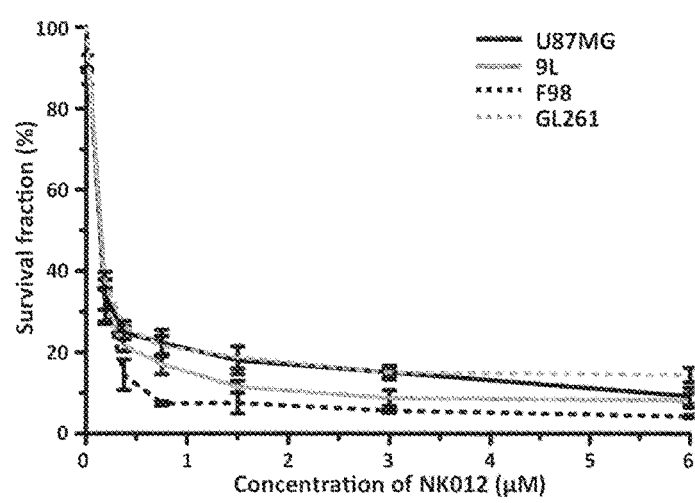
FIG. 1 is a graph showing in vitro growth inhibitory activity of NK012 in human, rat, and mouse glioma cells.

The present invention is carried out by the following procedures.

Materials and Methods

Drugs and Cell Lines

SN-38 was purchased from Sigma-Aldrich Co. (St. Louis, Mo.) and was dissolved in dimethyl sulfoxide (Sigma-Aldrich Co.) at 40 mg/ml as stock solution. NK012 was provided by Nippon Kayaku Co., Ltd. (Tokyo, Japan). Infusion solution was prepared with 5% glucose solution. The human glioblastoma cell line U87MG, rat gliosarcoma cell line 9L and glioblastoma cell line F98, and mouse glioma cell line GL261 (American Type Culture Collection, Rockville, Md.) were cultured in essential medium containing 10% fetal bovine serum (Invitrogen, Carlsbad, Calif.) and 1% penicillin/streptomycin (Invitrogen) at 37° C. in the presence of 5% $CO_2$.

In Vitro Cytotoxicity Assay

In vitro cell proliferation was measured by the water soluble tetrazolium (WST) assay. Briefly, cells ($5 \times 10^3$ cells/well) were plated in 96-well plates in triplicate, allowed to attach for 24 hours, and then the growth medium was changed to new medium containing various concentrations of NK012. After incubation for 72 hours, 10% of WST-8 working solution (Cell Counting Kit-8®; Dojindo Molecular Technologies, Inc., Kumamoto, Japan) was added to each well followed by incubation for 1 hour. The absorbance at 450 nm was then measured in a 96-well spectrophotometric plate reader (SpectraMax 190; Molecular Devices, Sunnyvale, Calif.). Cell viability was measured in triplicate and was repeated 3 times. Data were averaged and normalized against the non-treated controls to generate dose-response curves. The number of living cells was calculated using the following formula:

% Control=(each absorbance−absorbance of blank well)/absorbance of control well×100.

Animals

Twelve-week-old male Fischer 344 rats were purchased from Japan SLC, Inc. (Hamamatsu, Shizuoka, Japan). Eight-week-old male athymic nude rats (F344/NJc1-rnu/rnu) were purchased from CLEA Japan, Inc. (Tokyo, Japan). Protocols used in the animal studies were approved by the Institute for Animal Experimentation of Tohoku University Graduate School of Medicine.

Intracranial Tumor Implantation

Fischer 344 rats were used for the 9L model, and F344/NJc1-rnu/rnu (nude) rats were used for the U87MG model. The 9L and U87MG cells were obtained as described previously (see Saito R, Bringas J R, Panner A, et al. Convection-enhanced delivery of tumor necrosis factor-related apoptosis-inducing ligand with systemic administration of temozolomide prolongs survival in an intracranial glioblastoma xenograft model. *Cancer Res.* 2004; 64(19): 6858-6862). Briefly, 9L and U87MG cells were harvested using trypsin-EDTA following washing once with complete medium, and resuspended in cold phosphate-buffered saline (PBS) for implantation. A cell suspension containing $1 \times 10^4$ (9L) or $2 \times 10^5$ (U87MG) cells per 10 μl of PBS was used for implantation into the striatum region of rat brains. Under deep isoflurane anesthesia, rats were placed in a small animal stereotactic frame (David Kopf Instruments, Tujunga, Calif.). A sagittal incision was made through the skin to expose the cranium, and a burr hole was made in the skull at 0.5 mm anterior and 3 mm lateral from bregma using a small dental drill. Five microliters of cell suspension were injected at a depth of 4.5 mm from the brain surface. After a wait of 2 minutes, another 5 µl were injected at a depth of 4 mm. After a final wait of 2 minutes, the needle was removed, and the wound was closed with sutures.

CED

Infusion was performed using the CED method as described previously (see Saito R, Bringas J R, McKnight T R, et al. Distribution of liposomes into brain and rat brain tumor models by convection-enhanced delivery monitored with magnetic resonance imaging. *Cancer Res.* 2004; 64(7): 2572-2579. Also, see Kikuchi T, Saito R, Sugiyama S, et al. Convection-enhanced delivery of polyethylene glycol-coated liposomal doxorubicin: characterization and efficacy in rat intracranial glioma models. *J Neurosurg.* 2008; 109 (5):867-873). Briefly, a reflux-free step-design infusion cannula connected to a 1-ml syringe mounted on a microinfusion pump (BeeHive; Bioanalytical System, West Lafayette, Ind.) was used to control the infusion rate. Under deep isoflurane anesthesia, the rats were placed in small-animal stereotactic frames (Narishige Co., Tokyo, Japan). A sagittal incision was made to expose the cranium followed by a burr hole in the skull positioned at 0.5 mm anterior and 3 mm lateral from the bregma using a small dental drill. The following ascending infusion rates were applied to achieve 20 µl total infusion volume: 0.2 µl/min for 15 minutes, 0.5 µl/min for 10 minutes, and 0.8 µl/min for 15 minutes.

Evaluation of NK012 and SN-38 Distribution in Rat Brain Tissue by Fluorescence Microscopy Normal Fischer 344 rats (three rats in each group) received CED using NK012 and free SN-38 (20 µl solution of 2 mg/ml SN-38 equivalent), and were euthanized immediately after CED. Serial coronal tissue sections (20 µm thickness) were prepared using Tissue-Tek Cryo3 (Sakura Finetek USA, Inc., Torrance, Calif.), and frozen sections were examined under a fluorescence microscope, BIOR-EVO BZ9000 (Keyence, Osaka, Japan), at an excitation wavelength of 377 nm and an emission wavelength 447 nm to evaluate the distribution of NK012 within the tissues. Image data were recorded using BZ-II Analyzer 1.10 software (Keyence).

Toxicity Evaluation of NK012

Four healthy male Fisher 344 rats weighting approximately 250 g received CED using NK012 (20 µl solution of 2.0 mg/ml free SN-38 equivalent). Rats were monitored daily for survival and general health, including alertness, grooming, feeding, excreta, skin, fur, mucous, membrane conditions, ambulation, breathing, and posture. Rats were deeply anesthetized with diethyl ether, and transcardially perfused with 0.9% saline followed by cold 4% paraformaldehyde 14 days after CED treatment. The brains were removed, post-fixed overnight in the same fixative at 4° C., subjected to paraffin sectioning (4 µm), and histologically examined with hematoxylin and eosin staining.

Survival Study Against the 9L and U87MG Orthotopic Brain Tumor Models

Twenty rats with implanted 9L tumor cells were randomly divided into three groups on day 5 after tumor cell implantation and treated as follows: (1) CED of PBS (n=7) as a control, (2) CED of free SN-38 (n=7), and (3) CED of NK012 (n=6). Fourteen rats with implanted U87MG tumor cells were randomly divided into two groups on day 5 after tumor cell implantation and treated as follows: (1) CED of PBS (n=7) as a control, and (2) CED of NK012 (n=7). CED infusion consisted of 20 µl of 5% glucose in the control groups, 40 µg of NK012 in 20 µl of 5% glucose in the NK012 groups, and 40 µg of free SN-38 in a solution of 50% dimethyl sulfoxide in 20 µl of 5% glucose in the SN-38 group. All other rats were monitored daily for survival. Survival was compared between the treatment groups using a log-rank test. Estimated survival was expressed as a Kaplan-Meier curve.

Gadolinium (Gd) Co-Infusion to Visualize NK012 Distribution

Six rats received 20 µl of Gd-diethylenetriaminepentaacetic acid (5 mM) co-infused with 2 mg/ml of NK012 into the striatum. MRI was performed approximately 1 hour after the infusion using a 7.0-tesla PharmaScan System (Bruker Biospin, Karlsruhe, Germany) with a 38-mm diameter birdcage coil. Each rat was initially anesthetized with 4% isoflurane and an air/oxygen mixture (7:3). The isoflurane level was lowered to 2.0±0.5% during the MRI. Throughout the MRI, the animal's body temperature was kept at 36±1° C. with a feedback-controlled warm air system (SA Instruments, Stony Brook, N.Y.). The respiration and rectal temperatures were continuously monitored with a small animal monitoring system (SA Instruments). To investigate the relationship between distribution volume of NK012 and Gd at the infusion site, the MR image-based distribution volumes of Gd were calculated with OsiriX (OsiriX Foundation, Geneva, Switzerland) using threshold-based segmentation to grow three-dimensional regions of interest (ROIs) with human-entered seed points. The lower threshold employed was increased by 60% of the maximum on the contralateral side. The "Grow Region (2D/3D segmentation)" tool in the "ROI" dropdown menu allowed automatic outlining of the Gd distribution.

For histological evaluation of NK012 distribution, the rats were euthanized immediately after each MRI session. The brains were harvested, freshly frozen using ice-cold isopentane, and cut into serial coronal sections (20 µm) using a Tissue-Tek Cryo3 (Sakura Finetek USA, Inc.). The fluorescent signal generated by SN-38 was visualized with a fluorescence microscope, BIOREVO BZ9000 (Keyence), at an excitation wavelength of 377 nm and an emission wavelength of 447 nm to evaluate the distribution of NK012. Image data were recorded with BZ-II Analyzer 1.10 software (Keyence). The volume of the NK012 distribution was analyzed using ImageJ software. The volume of NK012 distribution, as determined by the fluorescence microscopy images, was compared with the volume of Gd distribution as detected by 7.0-tesla MRI.

Statistical Analysis

Statistical analysis was performed using GraphPad Prism 5 for Windows (GraphPad Software, Inc., San Diego, Calif.). All experiments were repeated three times and the differences for two sample comparisons were determined by the Student's t-test. Survival analyses were carried out using Kaplan-Meier curves and the log-rank test. Significance was determined at $P<0.05$.

Results

Efficacy of NK012 In Vitro

The WST assay showed that proliferation of the glioma cell lines, U87MG, 9L, F98, and GL261, were potently inhibited by NK012. The half maximal inhibitory concentrations of NK012 were 0.154, 0.196, 0.184, and 0.1511 µM for U87MG, 9L, F98, and GL261 cell lines, respectively (FIG. 1).

FIG. 1 indicates in vitro growth inhibitory activity of NK012 in human, rat, and mouse glioma cells. U87MG, 9L, F98, and GL261 cells were placed in 96-well plates and treated for 72 hours with various NK012 (0-6 μM) concentrations. After incubation for 72 hours, 10% of CCK-8 reagent was added to each well followed by incubation for 1 hour at 37° C., and then absorbance at 450 nm was measured in a 96-well spectrophotometric plate reader. Cell viability was measured in triplicate and was repeated 3 times. Data were averaged and normalized against the non-treated controls to generate dose-response curves.

Distribution of NK012 and SN-38 in Normal Rat Brain

Figure 2A:
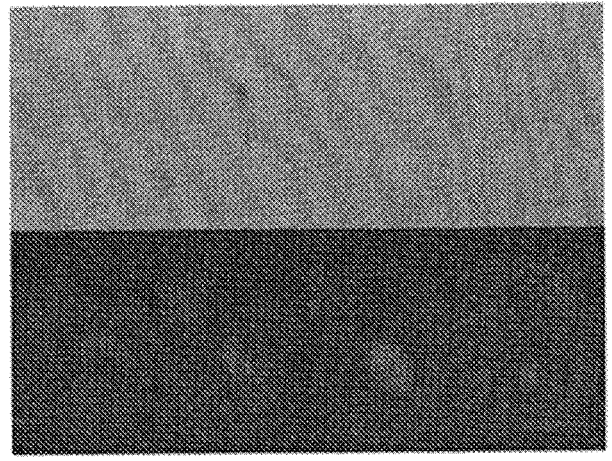
FIGS. 2A-C show an evaluation of the distribution of NK012 in normal rats.
Figure 2B:
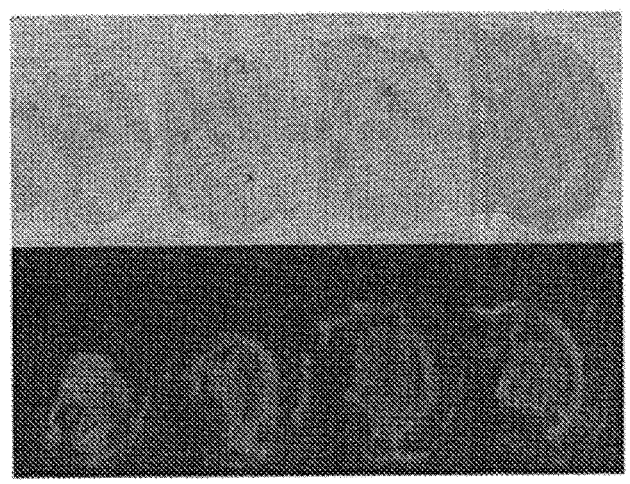
Figure 2C:
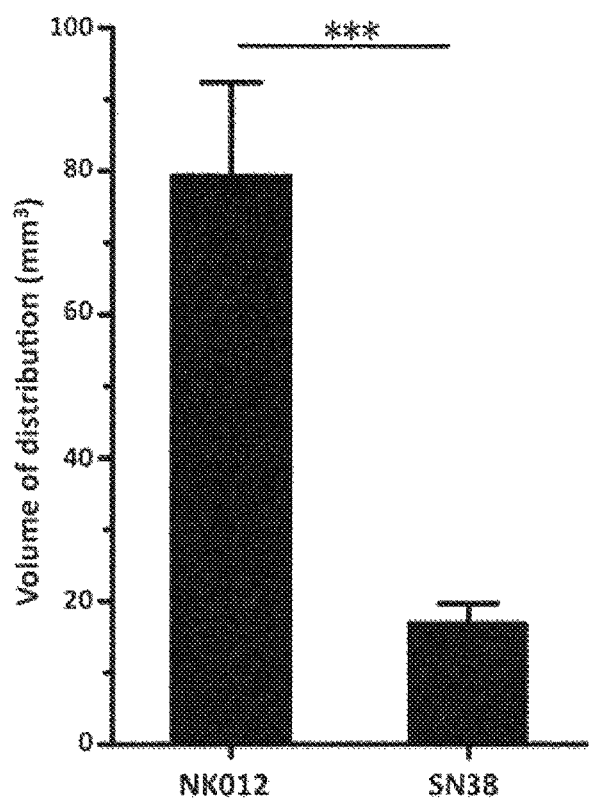

The distribution of free SN-38 (FIG. 2A) was quite restricted after CED into normal rat striatum, whereas the distribution of NK012 (FIG. 2B) was diffuse and extensive. FIG. 2A shows the distributions of free SN-38 (A), while FIG. 2B shows the distribution of NK012 (0.2 mg/ml; 20 μl) infused by CED into the striatum of rat brains. Animals were euthanized immediately after infusion and serial sections were obtained using a cryostat (20 μm thickness; 1 mm interval). Bright-field images reveal the brain tissue (upper row), and the same sections visualized with a fluorescence microscope detect the fluorescence generated from SN-38 under ultraviolet radiation (lower row). Serial images obtained from representative rats are shown in FIGS. 2A and 2B. The mean volumes of distribution of free SN-38 and NK012 were 17.00±2.65 and 79.39±12.99 mm$^3$, respectively (P<0.0001, FIG. 2C). Note that increased local brain damage was found in brains that received free SN-38.

Toxicity of NK012 in Normal Rat Brain

Figure 3:
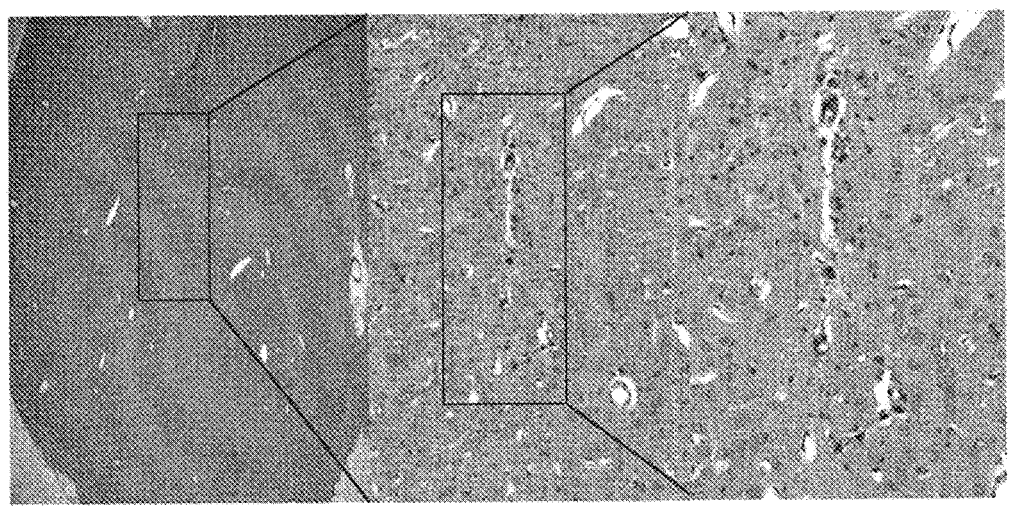
FIG. 3 shows representative histological changes in brain tissues after CED of 0.04 mg of NK012 as 2.0 mg/ml solution are infused locally into the intact striatum.

The rats that received CED infusion of 40 μg NK012 survived without neurological symptoms, and were euthanized on day 14 after CED. Brain sections (4 μm) were obtained for hematoxylin and eosin staining. Histological examination revealed only slight tissue damage at the needle tract (FIG. 3). Namely, rats survived without neurological symptoms and negligible tissue damage.

Figure 4A:
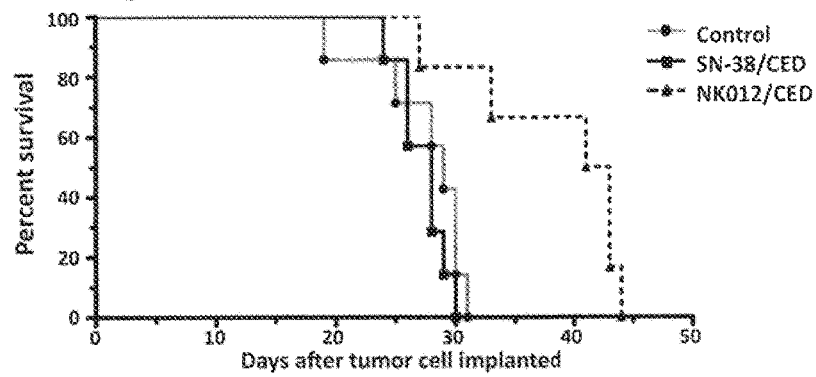
FIGS. 4A and 4B are graphs showing the effect of CED of NK012 on the rodent orthotopic brain tumor models.

Antitumor Efficacy of NK012 Delivered with CED in 9L and U87MG Orthotopic Brain Tumor Models First, the survival of rats with the 9L orthotopic brain tumor model was tested. Rats in the control group that received PBS were all euthanized at 19-31 days after tumor cell implantation due to neurological symptoms indicative of tumor progression (FIG. 4A). Median survival for this group was 29 days. Rats in the SN-38 group that received 0.04 mg SN-38 by CED were euthanized at 24-30 days after implantation due to tumor-related symptoms (median survival 28 days; P=0.2846, log-rank test). Rats in the NK012 group that received 0.04 mg NK012 with CED survived for 27-44 days. Median survival for this group was 42 days (P=0.0063 compared to the control group, P=0.0045 compared to the SN-38 group, log-rank test).

Figure 4B:
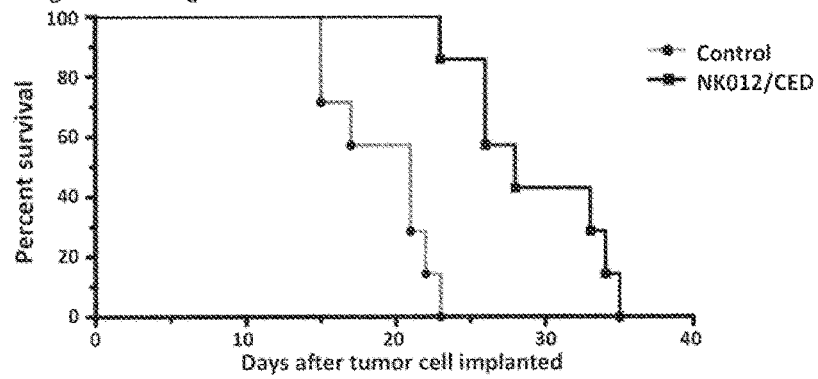

Subsequently, survival of rats with the U87MG brain tumor xenograft was tested. Rats in the control group were euthanized 15-23 days after implantation due to neurological symptoms indicative of tumor progression (median survival 21 days; FIG. 4B). Rats in the NK012 group were euthanized 23-33 days after tumor cell implantation (median survival 28 days). CED treatment with NK012 resulted in a significant survival benefit compared to the control (P=0.0003, log-rank test).

Correlation Between Volume of Distribution and Histological Analysis

Figure 5A:
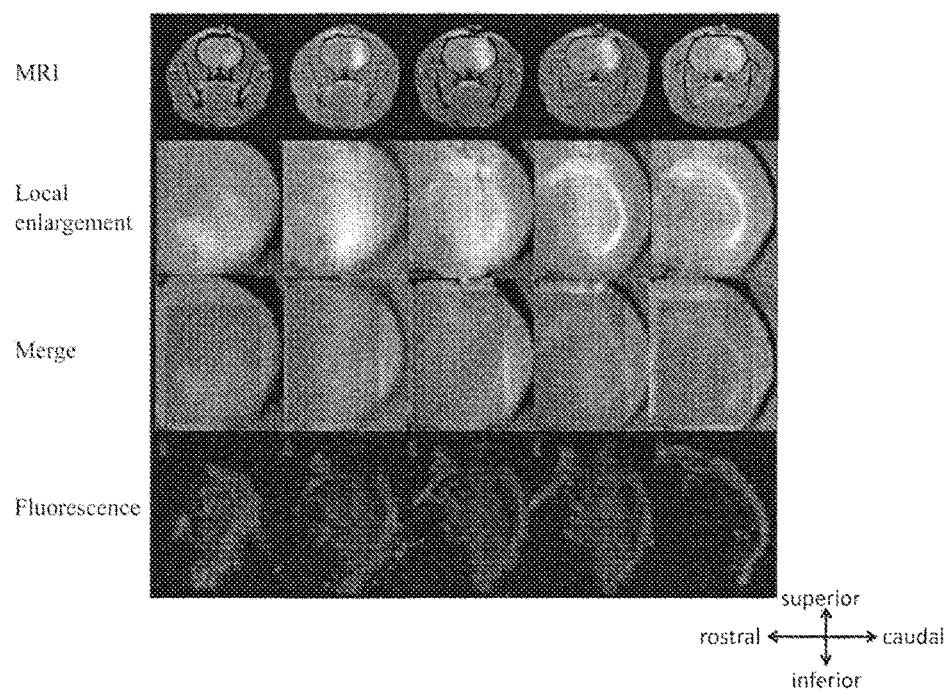
FIG. 5A shows a series of images including superimposed fluorescence and MR images of Gd co-delivered to the rat brain using CED.
Figure 5B:
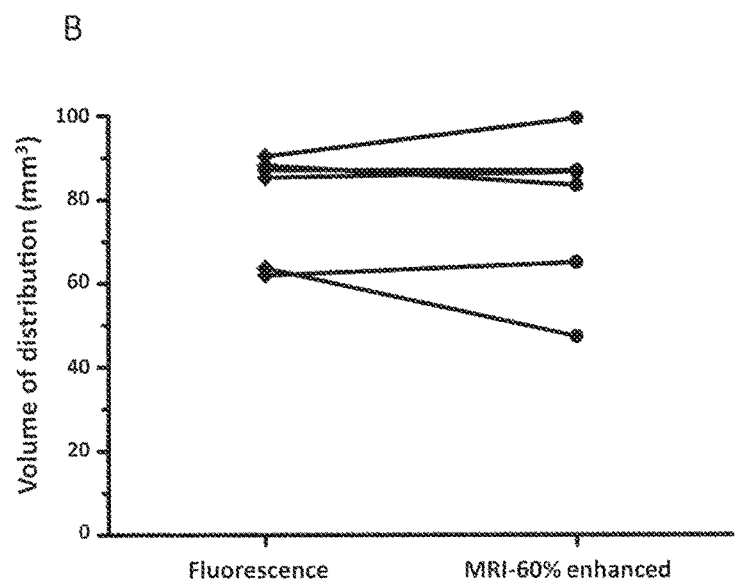
FIG. 5B is a graph showing the volume of distribution calculated based on MRI data and histological fluorescence data.

The tissue distribution of NK012 was consistent, so and was subsequently compared the distribution of co-infused Gd. The volume of NK012 distribution in a normal rat brain was determined by histological detection of fluorescence generated from SN-38. To assess the feasibility using MRI to monitor NK012 distribution in the rodent brain during CED, a Gd and NK012 mixture was infused with CED in six rats. Robust and clearly defined distributions of Gd were observed at each infusion site with T1-weighted MRI obtained immediately after infusion. Distribution volumes of Gd were automatically measured with OsiriX, an open source DICOM (Digital Imaging and Communications in Medicine) reader, using an imaging workstation. T1-weighted MRI demonstrated a close correlation between contrast-enhancement and NK012 distribution determined by histological detection of fluorescence generated from SN-38 (FIG. 5).

DISCUSSION

CED is a promising method for delivering therapeutic agents specifically into the targeted region of the CNS, but the PRECISE randomized phase III clinical trial employing CED failed to meet its clinical end points (see Kunwar S, Chang S, Westphal M, et al; PRECISE Study Group. Phase III randomized trial of CED of IL13-PE38QQR vs Gliadel wafers for recurrent glioblastoma. Neuro Oncol. 2010; 12(8):871-881). Although drug distribution was not assessed in that study, a retrospective analysis using BrainLAB iPlan® Flow software to estimate the expected drug distribution reported that the estimated coverage of the relevant target volumes, defined as the 2-cm penumbra of the resection cavity, was as low as 20.1% on average (see Sampson J H, Archer G, Pedain C, et al; PRECISE Trial Investigators. Poor drug distribution as a possible explanation for the results of the PRECISE trial. J Neurosurg. 2010; 113(2): 301-309). Therefore, poor drug distribution is a possible explanation for the failure of the PRECISE trial.

Distribution volume is a key property that affects the anti-tumor efficacy of therapeutic agents delivered by CED. However, locally applied agents with different physical and chemical properties have demonstrated different distribution volumes during CED into rodent brains (see Saito R, Krauze M T, Noble C O, et al. Tissue affinity of the infusate affects the distribution volume during convection-enhanced delivery into rodent brains: implications for local drug delivery. J Neurosci Methods. 2006; 154(1-2):225-232). Therefore, chemotherapeutic agents that are tested with CED should be formulated specifically to achieve the required distribution. The distribution characteristics of individual agents delivered by CED are difficult to evaluate, but the effectiveness of drug carriers such as liposomes and micelles was previously demonstrated. The efficacy of doxorubicin delivered in liposome or micelle formulation in the rodent brain tumor model has been already demonstrated (see Kikuchi T, Saito R, Sugiyama S, et al. Convection-enhanced delivery of polyethylene glycol-coated liposomal doxorubicin: characterization and efficacy in rat intracranial glioma models. J Neurosurg. 2008; 109(5):867-873. Also, see Inoue T, Yamashita Y, Nishihara M, et al. Therapeutic efficacy of a polymeric micellar doxorubicin infused by convection-enhanced delivery against intracranial 9L brain tumor models. Neuro Oncol. 2009; 11(2):151-157). Further investigations will search for clinically promising agents to be delivered by CED and for clinically relevant methods of delivery.

The anticancer plant alkaloid 7-ethyl-10-hydroxy-camptothecine (SN-38) is a broad spectrum anticancer camptothecin analogue which acts as a DNA topoisomerase I inhibitor. Irinotecan hydrochloride (CPT-11), a prodrug of SN-38, has shown some antitumor activities in patients with recurrent glioblastoma, with response rates of 0% to 17% in several trials (see Friedman H S, Petros W P, Friedman A H, et al. Irinotecan therapy in adults with recurrent or progressive malignant glioma. *J Clin Oncol.* 1999; 17(5):1516-1525. Also, see Cloughesy T F, Filka E, Kuhn J, et al. Two studies evaluating irinotecan treatment for recurrent malignant glioma using an every-3-week regimen. *Cancer.* 2003; 97(9 Suppl):2381-2386. Further, see Chamberlain M C. Salvage chemotherapy with CPT-11 for recurrent glioblastoma multiforme. *J Neurooncol.* 2002; 56(2):183-188. Furthermore, see Prados M D, Lamborn K, Yung W K, et al; North American Brain Tumor Consortium. A phase 2 trial of irinotecan (CPT-11) in patients with recurrent malignant glioma: a North American Brain Tumor Consortium study. *Neuro Oncol.* 2006; 8(2):189-193). The activity of CPT-11 depends on the conversion ratio of CPT-11 to SN-38. Thus, direct use of SN-38 might be effective for glioblastoma treatment, but clinical application has been limited because SN-38 is water-insoluble with high toxicity, so cannot be administered intravenously.

The present invention discloses that SN-38 infused by CED caused severe local tissue damage and distribution was quite restricted around the infusion site (FIG. 2A). In contrast, NK012 was consistently and extensively distributed by CED (FIG. 2B). Locally delivered NK012 had superior antitumor activity in the 9L orthotopic brain tumor model compared with SN-38, and the Kaplan-Meier analysis revealed a statistically significant difference compared with the SN-38 group (P=0.0045). In addition, histological examination revealed minimal brain tissue damage in rat brains that received 40 μg NK012, the same SN-38 dose that caused severe damage with free administration. Recently, it has been demonstrated that concentration rather than dose is the controlling factor in local tissue toxicity after extensive delivery with CED (see Zhang R, Saito R, Mano Y, et al. Concentration rather than dose defines the local brain toxicity of agents that are effectively distributed by convection-enhanced delivery. *J Neurosci Methods.* 2013; 222:131-137). Those findings suggest that a formulation of NK012 containing 2 mg/ml SN-38 or less is safe for CED application.

The present invention established a method of using MRI to monitor the CED of NK012 in the brain, to explore the clinically relevant applications of this CED-based therapy. A close correlation between the distributions of Gd and of NK012 was observed. Therefore, the distribution of NK012 can be monitored by co-delivery of Gd during CED and may have important implications in ensuring effective delivery of therapeutic agents into brain targets.

The present invention provides experimental evidence that NK012 can be efficiently administered into the brain by CED, with resultant activity against glioblastoma cells at concentrations lower than those causing dose-limiting systemic or neurological toxicity to the normal brain. The distribution of NK012 could be monitored by MRI of co-delivered Gd. Such NK012 administration by CED is a promising therapeutic approach to treat patients with glioblastoma.

INDUSTRIAL APPLICABILITY

The present invention, CED of NK012, is directed to an effective treatment option for intracranial brain tumor, particularly malignant gliomas. An MRI-guided CED of NK012 has a potential for clinical applications.

What is claimed is:

1. A method for delivering NK012 to a subject, comprising the step of:
   administering the NK012 into a central nervous system of the subject via a convection-enhanced delivery system, wherein
   the NK012 is a preparation comprising SN-38-loaded polymeric micelles.

2. The method according to claim 1, wherein the convection-enhanced delivery system is an osmotic pump.

3. The method according to claim 1, wherein the convection-enhanced delivery system is an infusion pump.

4. The method according to claim 1 wherein the subject is a human.

5. The method according to claim 1, wherein the NK012 is administered into a brain of the subject.

6. A method for delivering NK012 to a subject having an intracranial brain tumor, comprising the step of:
   administering the NK012 into a central nervous system of the subject via a convection-enhanced delivery system,
   wherein the NK012 is a preparation comprising SN-38-loaded polymeric micelles, which comprise SN-38 and block copolymer.

7. The method according to claim 6, wherein the intracranial brain tumor is a malignant glioma.

8. A method for using a convection-enhanced delivery system in a subject, comprising the step of:
   delivering NK012 to a cranial cavity of the subject via the convection-enhanced delivery system, wherein
   the NK012 is a preparation containing SN-38-loaded polymeric micelles.

9. The method according to claim 8, wherein the convection-enhanced delivery is an osmotic pump or an infusion pump.

* * * * *